(12) United States Patent
Okamoto et al.

(10) Patent No.: US 8,858,829 B2
(45) Date of Patent: Oct. 14, 2014

(54) CYCLOHEXANE COMPOUND AND LIQUID CRYSTAL COMPOSITION CONTAINING THE SAME

(75) Inventors: Kazuo Okamoto, Omaezaki (JP); Toshihiro Shibata, Saitama (JP)

(73) Assignees: Organo Science Co., Ltd., Omaezaki-Shi (JP); Chiracol Co., Ltd., Saitama, Saitama (JP)

( * ) Notice: Subject to any disclaimer, the term of this patent is extended or adjusted under 35 U.S.C. 154(b) by 0 days.

(21) Appl. No.: 13/634,942

(22) PCT Filed: Jun. 30, 2011

(86) PCT No.: PCT/JP2011/065112
§ 371 (c)(1),
(2), (4) Date: Dec. 4, 2012

(87) PCT Pub. No.: WO2012/011375
PCT Pub. Date: Jan. 26, 2012

(65) Prior Publication Data
US 2013/0092875 A1    Apr. 18, 2013

(30) Foreign Application Priority Data

Jul. 17, 2010 (JP) ................................. 2010-162348
Sep. 27, 2010 (JP) ................................. 2010-214647
Jan. 29, 2011 (JP) ................................. 2011-017322

(51) Int. Cl.
| | |
|---|---|
| *C09K 19/06* | (2006.01) |
| *C09K 19/00* | (2006.01) |
| *C09K 19/52* | (2006.01) |
| *C07C 19/08* | (2006.01) |
| *C07C 22/00* | (2006.01) |
| *C07C 25/13* | (2006.01) |
| *C07C 49/00* | (2006.01) |
| *C07C 43/18* | (2006.01) |
| *C07C 35/21* | (2006.01) |
| *C07C 49/577* | (2006.01) |
| *C07C 43/172* | (2006.01) |
| *C07C 25/18* | (2006.01) |
| *C07C 43/12* | (2006.01) |
| *C07C 49/517* | (2006.01) |
| *C07C 49/557* | (2006.01) |
| *C07C 17/16* | (2006.01) |
| *C09K 19/04* | (2006.01) |
| *C07C 49/417* | (2006.01) |
| *C07C 23/18* | (2006.01) |
| *C09K 19/30* | (2006.01) |

(52) U.S. Cl.
CPC ..... *C09K 19/3003* (2013.01); *C09K 2019/3004* (2013.01); *C07C 49/577* (2013.01); *C07C 43/172* (2013.01); *C07C 25/18* (2013.01); *C07C 43/12* (2013.01); *C07C 49/517* (2013.01); *C07C 49/557* (2013.01); *C07C 17/16* (2013.01); *C07C 22/00* (2013.01); *C09K 19/0403* (2013.01); *C09K 2019/0466* (2013.01); *C07C 35/21* (2013.01); *C07C 49/417* (2013.01); *C07C 23/18* (2013.01); *C07C 2101/14* (2013.01)

USPC ................. 252/299.6; 252/299.01; 428/1.1; 568/367; 568/664; 568/816; 570/129; 570/130; 570/131; 570/188

(58) Field of Classification Search
USPC ............ 252/299.01, 299.6; 428/1.1; 570/101, 570/123, 129, 130, 131, 188; 568/367, 664, 568/816
See application file for complete search history.

(56) References Cited

U.S. PATENT DOCUMENTS

| | | | |
|---|---|---|---|
| 5,976,407 | A | 11/1999 | Tarumi et al. |
| 6,028,655 | A | 2/2000 | Weber et al. |
| 6,139,773 | A | 10/2000 | Kirsch et al. |
| 6,376,030 | B1 | 4/2002 | Heckmeier et al. |
| 6,475,595 | B1 | 11/2002 | Bremer et al. |
| 8,211,332 | B2 | 7/2012 | Hattori et al. |

FOREIGN PATENT DOCUMENTS

| | | |
|---|---|---|
| JP | 59-62533 A | 4/1984 |
| JP | 5-32971 A | 2/1993 |
| JP | 5-58926 A | 3/1993 |

(Continued)

OTHER PUBLICATIONS

Tanaka et al., "Synthesis of Nematic Liquid Crystal Compounds and Solid State Properties Thereof", Japanese Liquid Crystal Society, Proceedings of 12th Liquid Crystal Conference, Sep. 25, 1986, pp. 66-67, with English translation.

*Primary Examiner* — Geraldina Visconti
(74) *Attorney, Agent, or Firm* — Bacon & Thomas, PLLC

(57) ABSTRACT

The present invention intends to provide a novel cyclohexane compound that can form a liquid crystal composition of which response speed is improved when mixed with a nematic liquid crystal and the like and to provide a specified liquid crystal composition in which a novel cyclohexane compound is mixed. The novel cyclohexane compound is represented by the following formula (1).

[Formula 25]

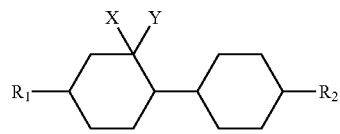

(1)

(In the formula (1), $R_1$ and $R_2$ represent the same or different R, ROCO or RCOO, and the R represents an alkyl group. The alkyl group may have an unsaturated bond, and, in the group, —$CH_2$— may be substituted with —O—, —CO— or —COO—, and a part of or an entirety of hydrogen atoms may be substituted with a halogen atom or a cyano group. X and Y each independently represents a halogen atom or a hydrogen atom and does not simultaneously represent a hydrogen atom. Further, alternatively, X represents an oxygen atom and Y represents a direct bond to the oxygen atom.)

8 Claims, No Drawings

(56) References Cited

FOREIGN PATENT DOCUMENTS

| | | | |
|---|---|---|---|
| JP | 5-279279 A | 10/1993 |
| JP | 5-320081 A | 12/1993 |
| JP | 6-56717 A | 3/1994 |
| JP | 7-17883 A | 1/1995 |
| JP | 7-126205 A | 5/1995 |
| JP | 9-31461 A | 2/1997 |
| JP | 10-46150 A | 2/1998 |
| JP | 2001-11456 A | 1/2001 |
| JP | 2007-91796 A | 4/2007 |

# CYCLOHEXANE COMPOUND AND LIQUID CRYSTAL COMPOSITION CONTAINING THE SAME

TECHNICAL FIELD

The present invention relates to a novel cyclohexane compound and a liquid crystal composition containing the new cyclohexane, and intends to improve the response speed of a liquid crystal display.

BACKGROUND ART

Many liquid crystal display devices that make use of the optical anisotropy (Δn) (hereinafter, referred to as "Δn" in some cases) or the dielectric constant anisotropy (Δ∈) (hereinafter, referred to as "Δ∈" in some cases), which are features of a liquid crystal compound, have been manufactured and have been used in watches, calculators, measurement instruments, instrument panels for vehicles, word processors, electronic diaries, portable telephones, printers, computers, TVs and so on. A liquid crystal compound used in liquid crystal display devices has a specific liquid crystal phase, and the phase mode thereof can be roughly divided into a nematic phase, a smectic phase and a cholesteric phase. Among these, a nematic phase is most widely used. Further, among display modes and driving systems, which are used in the display devices, as the display mode, a dynamic scattering mode (DS mode), a guest/host mode (GH mode), a twisted nematic mode (TN mode), a super-twisted nematic mode (STN mode), a thin-film transistor mode (TFT mode), and a ferroelectric liquid crystal mode (FLC mode) have been developed. As the driving systems, a static driving system, a multiplex driving system, an active matrix driving system, a two-frequency driving system and so on have been adopted. Recently, three kinds of the TN mode, STN mode and TFT mode are in a mainstream. A liquid crystal material used in any of display devices is necessary to be stable to moisture, air, heat, light and so on, in addition thereto, to show a liquid crystal phase in a temperature range as broad as possible around room temperature, have appropriate dielectric constant anisotropy (Δ∈) and refractive index anisotropy (Δn), be fast in the response speed, and be drivable at a low voltage. In order to satisfy these characteristics, a liquid crystal that is low in the viscosity and low in the threshold voltage is necessary. At the present time, as a single compound, there is no substance that can satisfy all the conditions mentioned above. Accordingly, liquid crystal compounds from several kinds to several tens kinds are mixed to obtain required characteristics. Further, for displays for high-definition TVs, 3D adaptable TVs and so on, a further improvement in the response speed is in demand.

There are many proposals also of a nematic liquid crystal composition that uses a cyclohexane compound and is excellent in the responsiveness. For example, a nematic liquid crystal composition that is large in a pretilt angle to be formed, remarkably low in the generation rate of stripe/domain, chemically stable, drivable at a low voltage and excellent in the high speed responsiveness capable of responding to a high time-sharing drive (patent document 1), and an antiferroelectric liquid crystal composition that is a novel cyclohexane compound that provides a nematic liquid crystal composition that is wide in an operative temperature range with respect to a magnitude of desired birefringent, and excellent in the responsiveness and contrast, and provides liquid crystal display devices such as TN-LCDs, STN-LCDs, TFT-LCDs and so on which use the nematic liquid crystal composition and are improved in the electrooptical properties, and is improved in the response speed from an antiferroelectric state to a ferroelectric state (patent document 2) can be cited. Further, there is a material of a liquid crystal display cell, which has a cyclohexane ring and, when mixed with a liquid crystal composition being generally used at the present time, does not shown an increase in the viscosity and can effectively reduce the threshold voltage (patent document 3). However, all proposals until now are unsatisfactory in the response speed.

PRIOR ART DOCUMENT

Patent Document

Patent document 1: JP Hei 06-56717 A
Patent document 2: JP Hei 07-126205 A
Patent document 3: JP Patent Application 2010-162348

The present inventors, after studying about cyclohexane compounds in a liquid crystal composition, have found a novel cyclohexane compound that can improve the response speed. Subsequently, the present inventors studied the response speed when the novel cyclohexane compound was mixed with a nematic liquid crystal compound having positive dielectric anisotropy and found a nematic liquid crystal composition that can further improve the response speed, further studied similarly also of the case where the novel cyclohexane compound was mixed with a nematic liquid crystal compound having negative dielectric anisotropy and found a nematic liquid crystal composition that can improve the response speed.

That is, a first object of the present invention is to provide a novel cyclohexane compound that, when mixed with a nematic liquid crystal or the like, can form a liquid crystal composition having improved response speed.

Then, a second object of the present invention is to mix the novel cyclohexane compound with a nematic liquid crystal compound having positive dielectric anisotropy and negative dielectric anisotropy to provide a nematic liquid crystal composition that further improves the response speed.

In the present specification, technical terms are used as shown below. A liquid crystal composition means a mixture of one kind or two or more kinds of compounds having a liquid crystal phase such as a nematic phase, a smectic phase or the like, and a mixture of one kind or two or more kinds of compounds having a liquid crystal phase and one kind or two or more kinds of compounds not having a liquid crystal phase. A liquid crystal display device means a liquid crystal display panel or a liquid crystal display module.

A compound of a formula (1) means one kind or two or more kinds of compounds represented by the formula (1), and two or more kinds of compounds may be referred to as a compound group. The same is true for a formula (2) and so on. Further, compound groups contained in the formula (1) are described as a formula (1-1) and a formula (1-2), and these are obtained by classifying the compound group belonging to the formula (1) according to a functional group and so on. When the compound group of the formula (1-1) is further classified, a formula (1-1-1) is used. In some cases, without describing as a formula (1), a formula (1-1) and so on, only (1), (1-1) and so on may be used. The same is true for the case of a formula (2) and so on.

SUMMARY OF THE INVENTION

Problem that the Invention is to Solve

The problem that the present invention is to solve is to provide a novel cyclohexane compound that can form, when mixed with a nematic liquid crystal or the like, a liquid crystal composition of which response speed is improved, and to provide a specified liquid crystal composition in which a novel cyclohexane compound is mixed.

Means for Solving the Problem

Firstly, a first invention relates to a cyclohexane compound represented by the following formula (1).

[Formula 1]

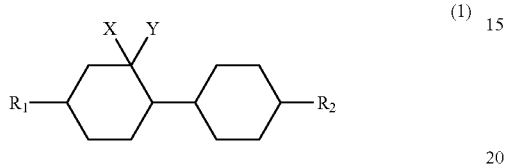
(1)

(In the formula, $R_1$ and $R_2$ represent the same or different R, ROCO, or RCOO, and the R represents an alkyl group. The alkyl group may have an unsaturated bond, and, in the group, —$CH_2$— may be substituted with —O—, —CO— or —COO—, and a part of or an entirety of hydrogen atoms may be substituted with a halogen atom or a cyano group. X and Y each independently represents a halogen atom or a hydrogen atom and does not simultaneously represent a hydrogen atom. Further, X represents an oxygen atom and Y represents a direct bond to the oxygen atom.)

In the formula (1) that represents a cyclohexane compound of the first invention, $R_1$ and $R_2$ represent the same or different R, RO, ROCO or RCOO. Examples of the alkyl groups represented by the R include methyl, ethyl, propyl, butyl, pentyl, hexyl, heptyl, octyl, nonyl, decyl, vinyl, allyl, butenyl, ethinyl, propynyl, butynyl, methoxymethyl, ethoxymethyl, propoxymethyl, butoxymethyl, methoxyethyl, ethoxyethyl, perfluoromethyl, perfluoroethyl, perfluoropropyl, monofluoromethyl, difluoromethyl, trifluoromethyl, perfluorovinyl, perfluoroallyl, isopropyl, 1-methylpropyl, 2-methylpropyl, 2-butylmethyl, 3-methylbutyl, 2-methylpentyl, 3-methylpentyl, 2-ethylhexyl, 2-propylpentyl, 1-methylpentyl and so on. $R_1$ and $R_2$ each is preferably a non-substituted alkyl group or a non-substituted alkenyl group.

A compound of the present invention represented by the formula (1) may exist as a mixture of a plurality of stereoisomers, and, in the case capable of being in a mode of cis-trans isomer, a trans-isomer is generally preferable.

Typical and specific examples of the cyclohexane compound groups of the first invention represented by the formula (1) include formulas (1-1) to (1-5) without restricting thereto. $R_1$ and $R_2$ in the formulas (1-1) to (1-5) that are compound groups of the formula (1) are the same as those in the formula (1).

[Formula 2]

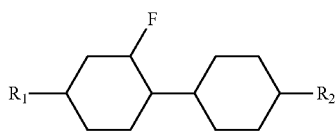
(1-1)

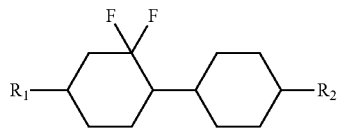
(1-2)

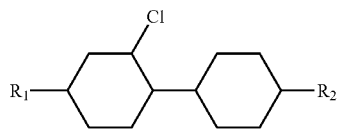
(1-3)

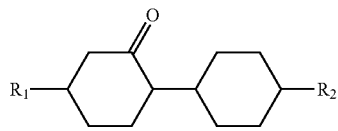
(1-4)

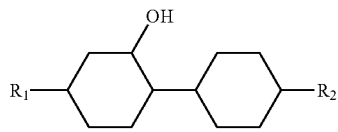
(1-5)

A method for manufacturing a cyclohexane compound of the formula (1) of the first invention is not restricted to a particular method. However, for example, a manufacturing method represented by the following scheme can be used to manufacture.

[Formula 3]

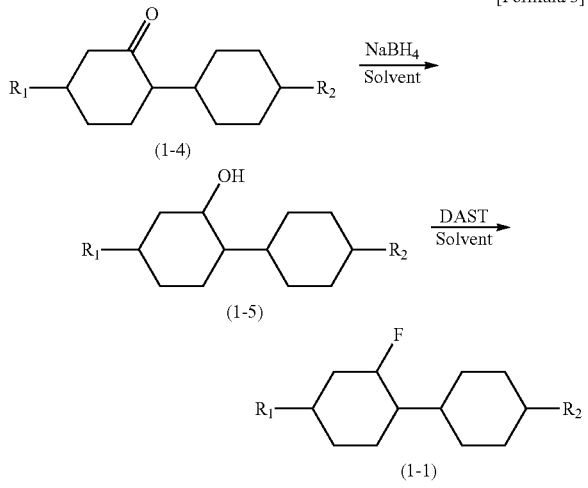

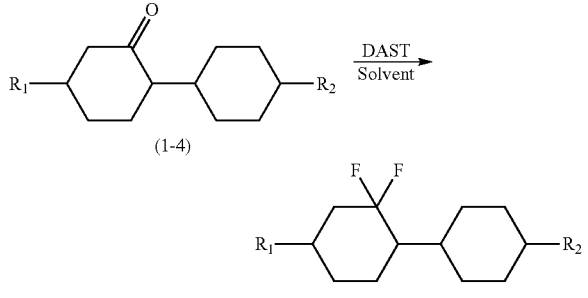

A compound of (1-4) can be obtained according to a known coupling reaction between

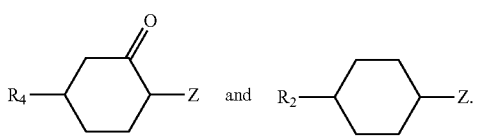

Z represents a halogen atom, and $R_1$ and $R_2$ are the same as those in the formula (1).

When a cyclohexane compound of the first invention is mixed with a known liquid crystal compound or a liquid crystal analogue or a mixture thereof (mother liquid crystal), a liquid crystal composition of the present invention is formed. Further, a liquid crystal composition of the present invention may be configured of only a cyclohexane compound of the present invention.

Subsequently, a second invention relates to a liquid crystal composition that contains at least one kind of a compound of a cyclohexane compound group represented by a formula (1) of the first invention as a first component and at least one kind of a compound of the respective compound groups represented by the following formulas (2), (3) and (4) as a second component.

[Formula 4]

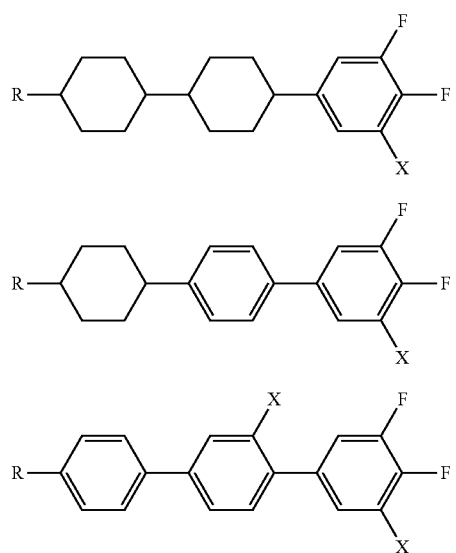

(In the formulas (2), (3) and (4), R represents an alkyl group, and X represents H or F.)

A liquid crystal composition of the second invention is a liquid crystal composition conditioned to contain at least one kind of a compound of a cyclohexane compound group of the formula (1) as a first component.

The second component is a liquid crystal composition obtained by combining at least one kind or more of compounds of the respective compound groups represented by the formulas (2), (3) and (4). That is, the second component contains each of at least one kind of a compound of the respective compound groups of the formulas (2) to (4). Then, when the first component and the second component are mixed to form a liquid crystal composition, the response speed can be improved.

Subsequently, a third invention relates to a liquid crystal composition in which at least one kind of a compound of a compound group represented by a formula (5) is mixed with the liquid crystal composition of the second invention at an optional ratio.

[Formula 5]

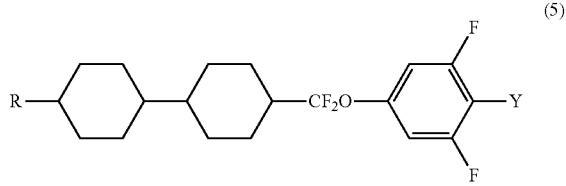

(In the formula (5), Y represents a F atom or $OCF_3$, and R represents an alkyl group.)

Also the compound group of the formula (5) has a function of reducing the viscosity of a liquid crystal composition to improve the response speed; accordingly, when mixing the compound, the response speed may be improved.

Next, a fourth invention relates to a liquid crystal composition that contains at least one kind of a compound of a cyclohexane compound group represented by a formula (1) of the present invention as a first component and at least one kind of a compound group of the respective compound groups represented by formulas (6), (7) and (8) as a second component.

A compound group of the formula (6) in the second component is shown below.

[Formula 6]

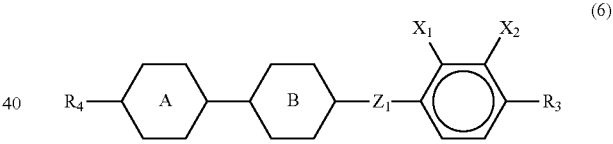

In the formula (6), $R_3$ and $R_4$ independently represent $C_1$ to $C_{12}$ alkyl, $C_1$ to $C_{22}$ alkoxy, $C_2$ to $C_{12}$ alkenyl, $C_2$ to $C_{11}$ alkenyloxy, or $C_2$ to $C_{12}$ alkyl or alkenyl where any of hydrogens is substituted with fluorine (the same is true for the following formulas (7) and (8)), a ring A and a ring B independently represent a cyclohexyl group or a phenyl group, $X_1$ and $X_2$ independently represent fluorine or chlorine, and $Z_1$ independently represents ethyleneoxy, carbonyloxy, ethylene or a single bond.

A compound group of the formula (7) in the second component is shown below.

[Formula 7]

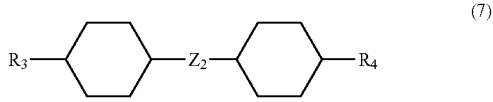

In the formula (7), $Z_2$ represents a single bond or ethylene.

A compound group of the formula (8) in the second component is shown below.

[Formula 8]

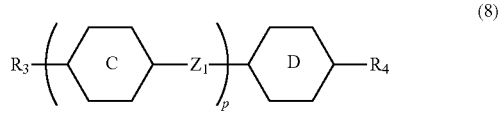

(8)

In the formula (8), a ring C and a ring D independently represent 1,4-cyclohexylene, 1,4-phenylene, 2-fluoro-1,4-phenylene, or 3-fluoro-1,4-phenylene, when p is 1, the ring D is 1,4-phenylene, and Z1 independently represents a single bond, ethylene, methyleneoxy, or carbonyloxy. P represents a numerical value of 1, 2 or 3.

A compound represented by the formula (1) of the first invention is a compound having slightly negative dielectric anisotropy. When the compound is mixed with a compound of the formula (6), which is a nematic liquid crystal material having large negative dielectric anisotropy, the response speed can be largely improved. Further, a compound of the formula (7) that can be expected to have an effect the same as that of the formula (1) can be added. Further, to a liquid crystal composition having negative dielectric anisotropy, which configures the present invention, for example, the formula (1), (1)+(6), (1)+(6)+(7), a compound represented by the formula (8) can be added to control the refractive index anisotropy and the liquid crystal temperature range.

Next, a fifth invention relates to a liquid crystal composition where the liquid crystal composition of the third invention is mixed with at least one kind of a compound of a compound group of the formula (7) of the fourth invention.

The compound group of the formula (7) has a function of reducing the viscosity of a liquid crystal composition to improve the response speed in a manner similar to that of the cyclohexane compound group of the formula (1). Accordingly, the liquid crystal composition of the third invention may be mixed with the compound group of the formula (7).

A sixth invention relates to a liquid crystal composition that contains one or two or more kinds of the cyclohexane compound groups of the formula (1) described in the first invention.

As described above, the compound of the formula (1) of the first invention is a compound having slightly negative dielectric anisotropy, and a liquid crystal composition is obtained by containing one or two or more kinds of the compound groups.

Then, a seventh invention relates to use of the liquid crystal composition described in any one of the first invention to the sixth invention in electrooptical applications.

Subsequently, an eighth invention relates to an electrooptical display device obtained by encapsulating a liquid crystal composition according to any one of the first invention to the sixth invention in a liquid crystal cell.

Effect of the Invention

The first invention provides a novel cyclohexane compound that can form, when mixed with a nematic liquid crystal or the like, a liquid crystal composition of which response speed is improved. The second and third inventions specify a nematic liquid crystal having positive dielectric anisotropy, which is mixed with the novel cyclohexane compound of the first invention, and the fourth and fifth inventions specify a nematic liquid crystal having negative dielectric anisotropy, which is mixed with the novel cyclohexane compound to further improve the response speed. The sixth invention makes the novel cyclohexane compound itself a liquid crystal composition, and the seventh and eighth inventions specify use thereof to promote the use of the present invention.

MODE FOR CARRYING OUT THE INVENTION

In what follows, a cyclohexane compound of the first invention will be described with reference to examples. However, the present invention is not restricted by the following examples.

Percentage represents percent by weight. All temperatures are represented by degree centigrade. The NI temperature represents a nematic phase-isotropic phase transition temperature, and Δn represents optical anisotropy (589 nm, 25° C.). The Δn was determined according to an extrapolation method after measuring a liquid crystal composition obtained by adding 10% of a compound of the present invention to the following mother liquid crystal D.

A mixture of the following three kinds of compounds was adopted as the mother liquid crystal D.

[Formula 9]

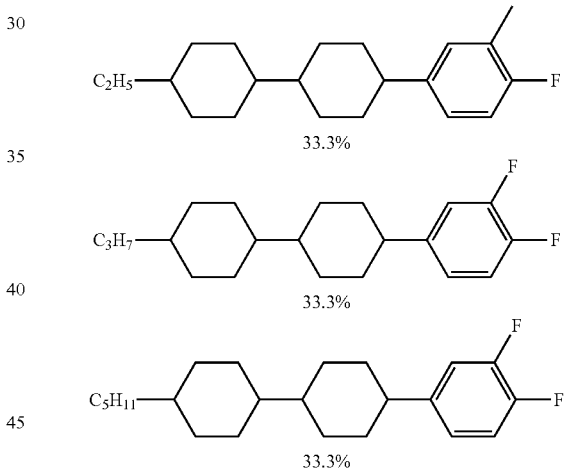

EXAMPLE 1

Synthesis Method of Compound of the Following Compound (1-4-1) Among Compound Group Represented by the Formula (1-4).

Firstly, 2-chloro-5-ethylhexanone and magnesium 4-n propyl cyclohexyl chloride were allowed to react in a diethyl ether or THF solvent under the presence of zinc chloride and copper (II) acetylacetonate, followed by applying a standard process, thereby a compound 1-4-1 was obtained.

Δn=0.059, m/z=250

Compounds from the following formulas (1-4-2) to (1-4-4) can be synthesized in a manner similar to that of the compound of the formula (1-4-1).

[Formula 10]

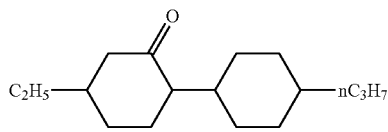 (1-4-1)

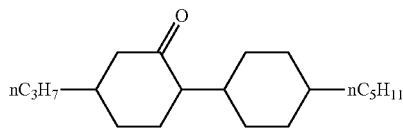 (1-4-2)

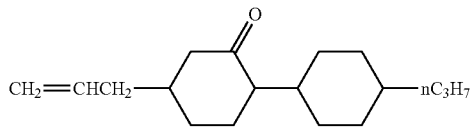 (1-4-3)

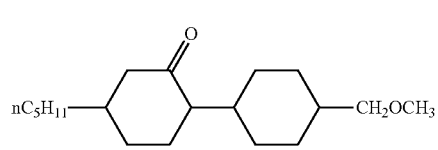 (1-4-4)

EXAMPLE 2

Synthesis Method of Compound of Formula (1-1-1) Shown Below

To 12 ml of isopropanol, 2.12 g of a compound of the formula (1-4-1) and 0.8 g of NaBH$_4$ were added and the mixture was heated for 32 hr under reflux. After that, toluene extraction was applied and a silica gel column treatment (heptane/ethyl acetate=5/1) was conducted, thereby a compound of a formula (1-5-1) shown below was obtained.

Next, 0.82 g of the compound of the formula (1-5-1) was dissolved in 8 ml of dichloromethane, therein 0.56 g of DAST was added at 4° C., followed by stirring for 28 hr at room temperature. The reaction mixture was poured into ice water, followed by extracting with dichloromethane. Silica gel column treatment (heptane: 100%) and Kugelrohr distillation were conducted, thereby 0.3 g of a compound of the formula (1-1-1) that is a target substance was obtained.

Δn=0.067, m/z=254

Compounds from the following formula (1-5-2) to (1-5-3) can be synthesized in a manner similar to that of the compound of the following formula (1-5-1).

[Formula 11]

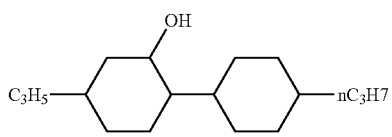 (1-5-1)

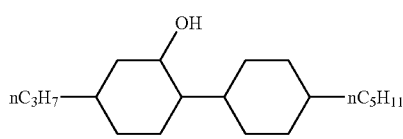 (1-5-2)

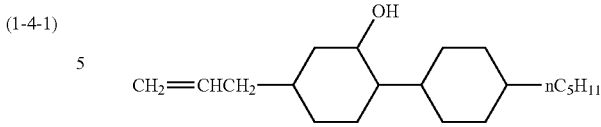 (1-5-3)

Further, also compounds from formulas (1-1-2) to (1-1-10) can be synthesized in a manner similar to that of the compound of the formula (1-1-1).

[Formula 12]

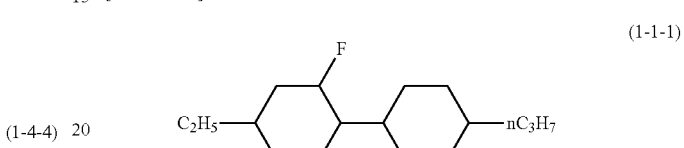 (1-1-1)

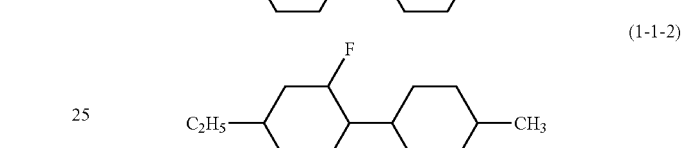 (1-1-2)

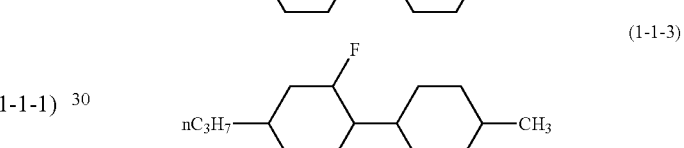 (1-1-3)

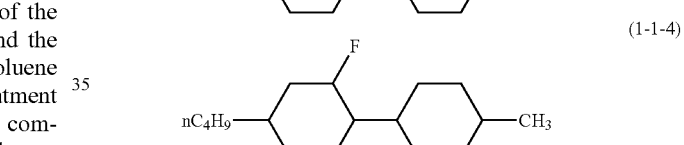 (1-1-4)

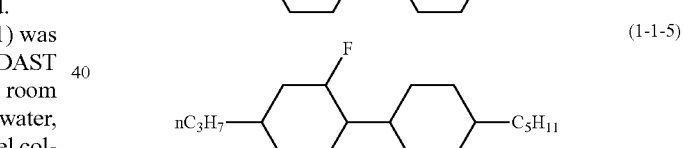 (1-1-5)

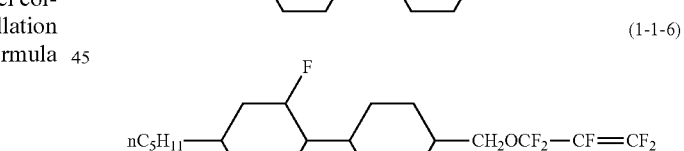 (1-1-6)

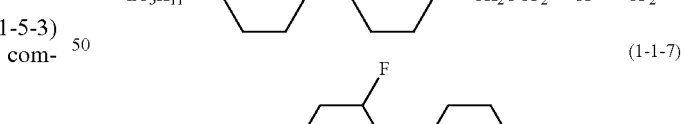 (1-1-7)

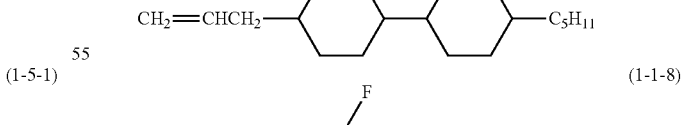 (1-1-8)

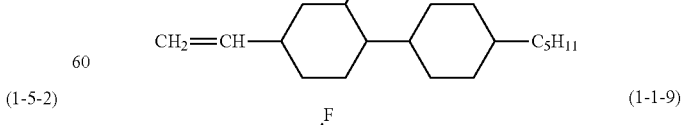 (1-1-9)

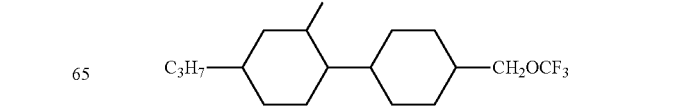

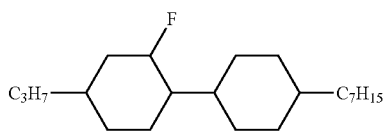
(1-1-10)

EXAMPLE 3

Synthesis Method of Compound of Formula (1-2-1) Represented by the Following Formula In 8 ml of dichloromethane, 0.5 g of a compound of the formula (1-4-1) was dissolved, therein 0.5 g of DAST was added at 4° C. Thereafter, the mixture was stirred for 38 hr at room temperature. After that, a treatment the same as that of example 2 was conducted, thereby 0.2 g of a compound of a formula (1-2-1) was obtained.

Δn=0.062, m/z=272

Compounds from formulas (1-2-2) to (1-2-9) can be synthesized in a manner similar to that of the compound of the formula (1-2-1).

[Formula 13]

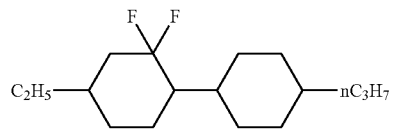
(1-2-1)

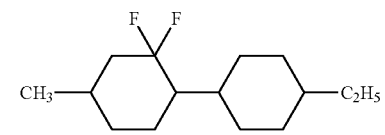
(1-2-2)

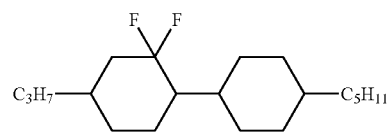
(1-2-3)

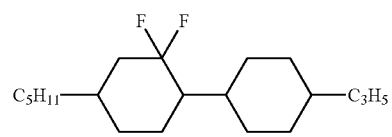
(1-2-4)

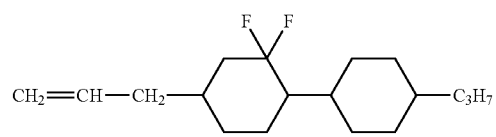
(1-2-5)

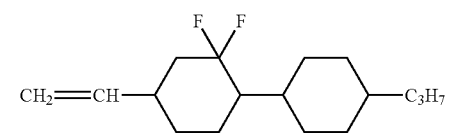
(1-2-6)

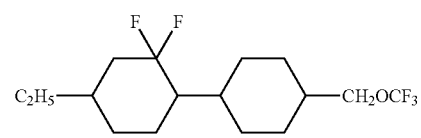
(1-2-7)

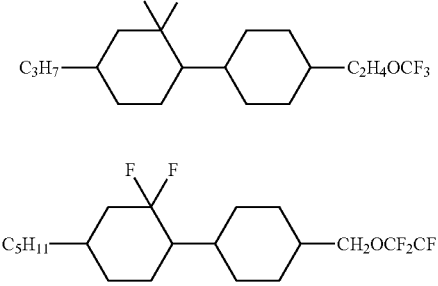
(1-2-8)
(1-2-9)

EXAMPLE 4

Synthesis Method of Compound of Formula (1-3-1) Shown Below

A compound of a formula (1-3-1) is synthesized according to a known synthesis method such as shown below.

[Formula 14]

(1-5-2)

(1-3-1)

In 10 ml of carbon tetrachloride (CCl$_4$), 0.8 g of a compound of the formula (1-5-2) and 2.0 g of TPP (triphenyl phosphine) were dissolved, and the mixture was heated for 25 hr under reflux. The generated triphenyl phosphine oxide was filtered and cleansed with heptane, thereafter, a standard treatment was conducted, further thereafter, a silica gel column treatment (heptane: 100%) was conducted, thereby 0.2 g of a compound of a formula (1-3-1) was obtained.

m/z=312

Also compounds from formulas (1-3-2) to (1-3-4) can be synthesized in a manner similar to that of the compound of the formula (1-3-1).

[Formula 15]

(1-3-1)

-continued

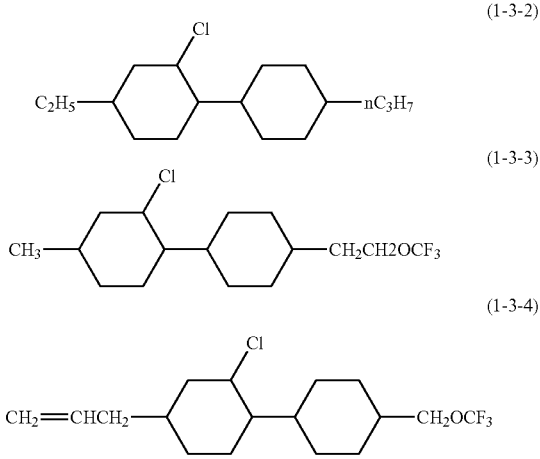

(1-3-2)

(1-3-3)

(1-3-4)

EXAMPLE 5

The electrooptical characteristics (response speed) of liquid crystal compositions 1, 2, and 3, which were obtained by adding 5 to 10% of the compounds of the formulas (1-1-2), (1-2-2) and (1-4-2) obtained according to examples 2, 3, and 4 to the mother liquid crystal D of the composition described above are shown in Table 1.

Table 1 shows switch-on times ($t_{on}$) and switch-off times ($t_{off}$) of the compositions under an operation voltage (rectangular wave) of 60 Hz±5 V.

TABLE 1

Response Speed of Each of the Composition

| No | Composition | Addition amount (%) | $t_{on}$ | $t_{off}$ |
|---|---|---|---|---|
| 1 | Composition 1 (1-1-2) | 10 | 6 msec | 13 msec |
| 2 | Composition 2 (1-2-2) | 5 | 6 msec | 15 msec |
| 3 | Composition 3 ((1-4-2) | 10 | 8 msec | 16 msec |
| 4 | Mother liquid crystal D | | 9 msec | 24 msec |

EXAMPLE 6

Nematic liquid crystals of the formulas (2) to (4) were mixed at a ratio shown below. This is a comparative example based on the second invention and referred to as comparative example 1.

TABLE 2

Comparative Example 1

| Compound | Mixing Ratio (%) |
|---|---|
| 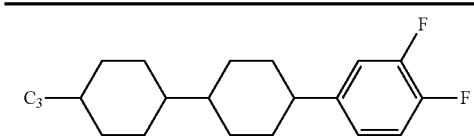 | 15 |

TABLE 2-continued

Comparative Example 1

| Compound | Mixing Ratio (%) |
|---|---|
| C₅–⟨cyclohexane⟩–⟨benzene⟩–⟨3,4,5-trifluorobenzene⟩ | 15 |
| C₃–⟨cyclohexane⟩–⟨benzene⟩–⟨3,4-difluorobenzene⟩ | 11 |
| C₅–⟨cyclohexane⟩–⟨benzene⟩–⟨3,4-difluorobenzene⟩ | 23 |
| C₃–⟨cyclohexane⟩–⟨cyclohexane⟩–⟨3,4,5-trifluorobenzene⟩ | 23 |
| C₃–⟨benzene⟩–⟨2-fluorobenzene⟩–⟨3,4,5-trifluorobenzene⟩ | 13 |

EXAMPLE 7

Table 3 shows a mixture of comparative example 1 of Table 2 and a cyclohexane compound of the formula (1-1-1) and this is referred to as example 1.

TABLE 3

Example 1

| Compound | Mixing ratio (%) |
|---|---|
| C₂H₅–⟨2-fluorocyclohexane⟩–⟨cyclohexane⟩–C₃H₇ (1-1-1) | 10 |
| Comparative example 1 | 90 |

EXAMPLE 8

Measurement results of the response speed of comparative example 1 and example 1 are shown in Table 4.

TABLE 4

Measurement Result of Response speed

| No | Sample | Rise time (msec) | Fall time (msec) |
|----|--------|------------------|------------------|
| 1 | Comparative example 1 | 3.2 | 11.7 |
| 2 | Example 1 | 3.0 | 5.7 |

The response speeds of Table 4 were the measured result of TN cells having a cell gap of 9 μm during application of input voltage of 10 V, offset voltage of 0.1 V and frequency of 100 Hz. The rise time means a time during which the dielectric constant rises from zero to 50% of the maximum dielectric constant when a voltage is turned on, and the fall time means a time during which the dielectric constant falls from the maximum dielectric constant to 50% thereof when a voltage is turned off. In Table 4, both of the rise time and fall time are represented by milliseconds (msec).

EXAMPLE 9

Among the compound group of the formula (6), the respective compounds of three kinds of formulas (6-1) to (6-3) shown below were mixed at the same weight and a mixed sample is referred to as comparative example 2.

[Formula 16]

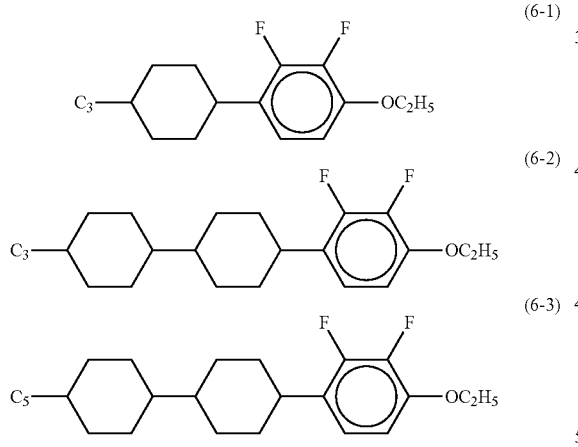

(6-1)

(6-2)

(6-3)

Then, among the compound group of the formula (7), a compound of a formula (7-1) shown below and the comparative example 2 were mixed at a weight ratio of 1:9 and this sample is referred to as comparative example 3.

[Formula 17]

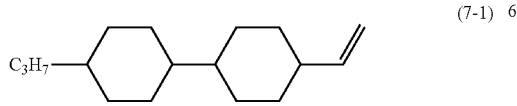

(7-1)

Mixing ratios of comparative example 2 and comparative example 3 are shown in Table 5.

TABLE 5

Mixing Ratio of Comparative Example 2 and Comparative Example 3

| Comparative example | Material to be mixed | Mixing ratio (weight) |
|---------------------|----------------------|------------------------|
| Comparative example 2 | Formula (6-1) | 1 |
| | Formula (6-2) | 1 |
| | Formula (6-3) | 1 |
| Comparative example 3 | Formula (7-1) | 1 |
| | Comparative example 2 | 9 |

Note:
A mixing ratio (weight ratio) of comparative example 2 is formula (6-1):formula (6-2):formula (6-3) = 1:1:1, and a mixing ratio (weight ratio) of comparative example 3 is formula (7-1):comparative example 1 = 1:9.

Formula (1-1-1) and formula (1-2-1), each of which is one kind of the cyclohexane compound group of the formula (1), are shown below. These compounds are mixed with comparative example 2, and mixtures are referred to as example 2 and example 3 and shown in Table 6.

[Formula 18]

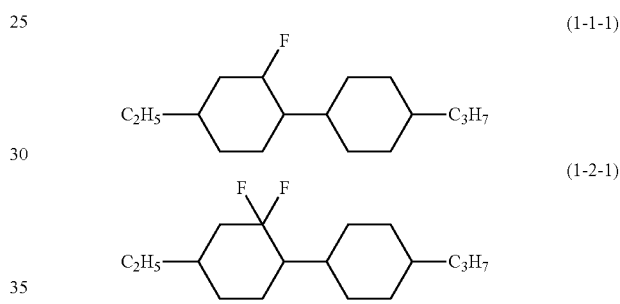

(1-1-1)

(1-2-1)

TABLE 6

Comparative Example 2 and Comparative Example 3

| Example | Material to be mixed | Mixing ratio (weight) |
|---------|----------------------|------------------------|
| Example 2 | Formula (1-1-1) | 1 |
| | Comparative example 2 | 9 |
| Example 3 | Formula (1-2-1) | 1 |
| | Comparative example 2 | 9 |

Note:
A mixing ratio (weight ratio) of example 2 is formula (1-1-1):comparative example 1 = 1:9, and a mixing ratio (weight ratio) of example 3 is formula (1-2-1):comparative example 1 = 1:9.

Measurement results of the response speed of comparative examples 2 and 3 and examples 2 and 3 are shown in Table 7.

TABLE 7

Response Speeds of Comparative Examples 2 and 3 and Examples 2 and 3

| Sample | Rise time (ms) | Fall time (ms) |
|--------|----------------|----------------|
| Comparative example 2 | 32 | 52 |
| Comparative example 3 | 26 | 32 |
| Example 2 | 20 | 25 |
| Example 3 | 21 | 29 |

The response speeds of Table 7 were the measured result of vertical gradient cells having a cell gap of 9 μm during application of input voltage of 10 V, frequency of 32 Hz and a rectangular wave of 300 msec. The rise time means a time during which the dielectric constant rises from zero to 50% of the maximum dielectric constant when a voltage is turned on, and the fall time means a time during which the dielectric constant falls from the maximum dielectric constant to 50% thereof when a voltage is turned off. In Table 7, both of the rise time and fall time are represented by milliseconds (msec).

INDUSTRIAL APPLICABILITY

In recent high-definition TVs, 3D adaptable displays and so on, a further improvement in the response speed is demanded. The present invention relates to a liquid crystal composition that can respond to such demands and is expected to be used in future.

The invention claimed is:

1. A cyclohexane compound represented by the following formula (1)

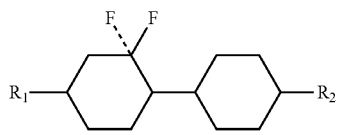
(1)

wherein $R_1$ and $R_2$ represent the same or different alkyl group(s), and wherein the group, —$CH_2$— may be substituted with —O—.

2. A liquid crystal composition comprising:
a first component comprising at least a cyclohexane compound represented by a formula (1) of claim 1; and
a second component comprising at least compound selected from the respective compound groups represented by the following formulas (2), (3) and (4),

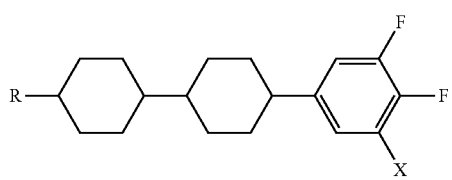
(2)

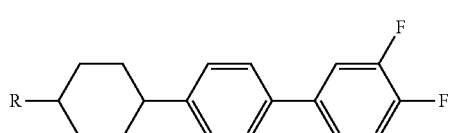
(3)

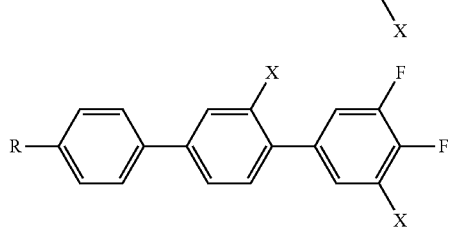
(4)

wherein R represents an alkyl group, and X represents H or F.

3. A liquid crystal composition comprising:
at least one compound represented by a formula (5), which is mixed with the liquid crystal composition of claim 2 at a specific ratio

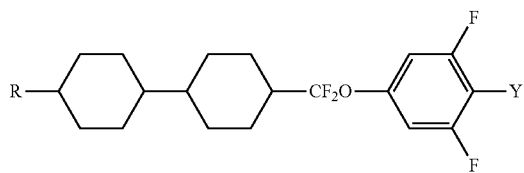
(5)

wherein Y represents a F atom or $OCF_3$, and R represents an alkyl group.

4. A liquid crystal composition comprising:
a first component comprising at least a cyclohexane compound represented by formula (1) of claim 1; and
a second component comprising at least one compound selected from the respective compound groups represented by formulas (6), (7) and (8),

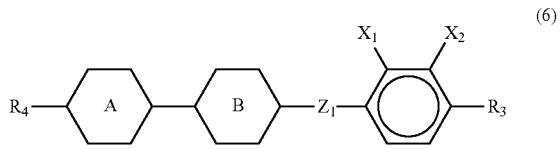
(6)

wherein $R_3$ and $R_4$ independently represent $C_1$ to $C_{12}$ alkyl, $C_1$ to $C_{12}$ alkoxy, $C_2$ to $C_{12}$ alkenyl, $C_2$ to $C_{11}$ alkenyloxy, or $C_2$ to $C_{12}$ alkyl or alkenyl group, where any of hydrogens is substituted with fluorine, a ring A and a ring B independently represent a cyclohexyl group or a phenyl group, $X_1$ and $X_2$ independently represent fluorine or chlorine, and $Z_1$ independently represents methyleneoxy, carbonyloxy, ethylene or a single bond,

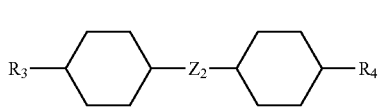
(7)

wherein $Z_2$ represents a single bond or ethylene,

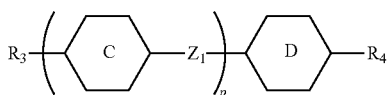
(8)

wherein a ring C and a ring D independently represent 1,4-cyclohexylene, 1,4-phenylene, 2-fluoro-1,4-phenylene, or 3-fluoro-1,4-phenylene, wherein when p is 1, the ring D is 1,4-phenylene, and Z1 independently represents a single bond, ethylene, methyleneoxy, or carbonyloxy when p represents 1, 2 or 3.

5. A liquid crystal composition comprising:
the liquid crystal composition of claim 3 mixed with at least one compound represented by the following general formula (7)

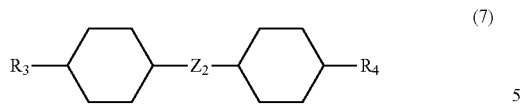
(7)

wherein $Z_2$ represents a single bond or ethylene, $R_3$ and $R_4$ independently represent $C_1$ to $C_{12}$ alkyl, $C_1$ to $C_{12}$ alkoxy, $C_2$ to $C_{12}$ alkenyl, $C_2$ to $C_{11}$ alkenyloxy, or $C_2$ to $C_{12}$ alkyl or alkenyl group, where any of hydrogens is substituted with fluorine.

6. A liquid crystal composition comprising:

two more cyclohexane compounds of claim 1.

7. An electrooptical display device comprising a cyclohexane compound described in claim 1.

8. An electrooptical display device comprising a cyclohexane compound of claim 1 encapsulated in a liquid crystal cell.

* * * * *